United States Patent
Sullivan (10) Patent No.: US 7,516,555 B2
(45) Date of Patent: Apr. 14, 2009

(54) SYSTEMS AND METHODS FOR FOOTWEAR RELATED MEASUREMENT AND ADJUSTMENT

(75) Inventor: Sean Sullivan, Aptos, CA (US)

(73) Assignee: Somnio, Inc., Aptos, CA (US)

( * ) Notice: Subject to any disclaimer, the term of this patent is extended or adjusted under 35 U.S.C. 154(b) by 0 days.

(21) Appl. No.: 12/130,250

(22) Filed: May 30, 2008

(65) Prior Publication Data
US 2009/0019713 A1 Jan. 22, 2009

Related U.S. Application Data

(63) Continuation-in-part of application No. 11/779,943, filed on Jul. 19, 2007, now Pat. No. 7,421,789.

(51) Int. Cl.
A43D 1/00 (2006.01)
A61B 5/103 (2006.01)

(52) U.S. Cl. .............................. 33/3 R; 33/512; 33/3 A; 33/3 B; 600/592

(58) Field of Classification Search .................... 33/3 R, 33/3 A, 3 B, 3 C, 511, 512, 515, 4, 5, 6, 806, 33/832, 300; 600/592
See application file for complete search history.

(56) References Cited

U.S. PATENT DOCUMENTS

| | | | |
|---|---|---|---|
| 2,535,787 A | 12/1950 | Darby | |
| 4,227,311 A | 10/1980 | Behney | |
| 4,662,079 A | 5/1987 | Graf et al. | |
| 4,669,142 A | 6/1987 | Meyer | |
| 4,756,096 A | 7/1988 | Meyer | |
| 4,807,368 A | 2/1989 | Beyl | |
| 4,821,420 A | 4/1989 | Maykel | |
| 5,689,446 A | 11/1997 | Sundman et al. | |
| 6,289,107 B1 * | 9/2001 | Borchers et al. | 600/592 |
| 7,069,665 B1 | 7/2006 | Adriano | |
| 7,082,697 B2 | 8/2006 | Ellis, III | |
| 7,125,509 B1 | 10/2006 | Smith | |
| 7,281,333 B2 | 10/2007 | Caulliez et al. | |
| 7,336,377 B2 * | 2/2008 | Danenberg et al. | 33/3 R |

(Continued)

OTHER PUBLICATIONS

Aline foot measuring device.
Brannock foot measuring device.

*Primary Examiner*—Yaritza Guadalupe-McCall
(74) *Attorney, Agent, or Firm*—Trent H. Baker; Baker & Associates PLLC (57) ABSTRACT

One embodiment of the present invention relates to a footwear characteristic measuring system designed to determine measurements of a particular footwear wedge insert which may be used to encourage correct knee alignment in an article of footwear. The system includes a base, a stepped member, a platform, and an illumination system. The stepped member or piano hinge is positioned on the top surface of the base adjacent to or partially under the platform. The platform is disposed above the top surface of the base and connected on a first side to the base via a hinge. A second portion of the platform is positioned on top of a portion of the stepped member so as to form a particular angle with respect to the base depending on the height of the particular stepped member surface. The illumination system is oriented to transmit an illumination output upward or perpendicular to the top surface of the base.

20 Claims, 8 Drawing Sheets

U.S. PATENT DOCUMENTS

| | | |
|---|---|---|
| 2003/0014881 A1 | 1/2003 | Hay |
| 2004/0193075 A1 | 9/2004 | Martindale |
| 2006/0080862 A1 | 4/2006 | Hay et al. |
| 2006/0227337 A1 | 10/2006 | Sundman et al. |
| 2006/0277772 A1 | 12/2006 | Pupko |
| 2006/0283243 A1 | 12/2006 | Peterson |
| 2007/0208278 A1 * | 9/2007 | Kohen-Raz ................. 600/592 |
| 2007/0253004 A1 | 11/2007 | Danenberg et al. |

* cited by examiner

SYSTEMS AND METHODS FOR FOOTWEAR RELATED MEASUREMENT AND ADJUSTMENT

RELATED APPLICATIONS

This is a continuation in part application claiming priority to U.S. utility application Ser. No. 11/779,943 filed Jul. 19, 2007 now U.S. Pat. No. 7,421,789, the contents of which are incorporated by reference.

FIELD OF THE INVENTION

The invention generally relates to footwear including shoes, boots, sandals, etc. In particular, the present invention relates to systems and methods for properly measuring, aligning, fitting, and adjusting feet and footwear.

BACKGROUND OF THE INVENTION

Footwear refers to articles worn on the foot of a user, including shoes, boots, sandals, etc. Footwear provides a supportive platform between the sole of user's foot and the ground to facilitate protection and alignment. For example, a pair of sandals protects a user's foot from abrasion and damage caused by debris or bacteria on the ground. In addition, a boot or shoe may support/align a user's foot and lower leg according to specific parameters. Footwear is generally designed to provide protection and support corresponding to a set of intended uses. For example, a trail running shoe is often designed to both protect and support a user's foot from conditions encountered while engaged in the activity of trail running. Protection refers to protecting both the skin and internal muscles of the foot. Alignment refers to maintaining or encouraging a user toward proper foot and body alignment.

One of the challenges of footwear design is the need to accommodate a wide variety of foot shapes and dimensions while providing a product that is economical. A second major challenge is the proper selection of an appropriate set of available footwear for a particular individual and activity. Human feet tend to encompass a wide variety of characteristics including volume, length, arch height, toe dimensions, and various protrusions. The variance in these characteristics causes people's feet to differ significantly from one another and sometimes from foot to foot. To properly provide optimal support characteristics, it is necessary for the article of footwear to correspond as closely as possible to the unique dimensions of a user's foot. An improperly-fitting article of footwear will likely cause pain, injury and damage to a user's foot, leg(s), back, and neck. Therefore, various systems and methods are used to facilitate selecting and/or adjusting existing footwear for a user.

Unfortunately, conventional measuring systems and methods fail to measure all of the variables necessary to select and/or adjust an article of footwear for optimal fit. One of the most common measuring devices measures only three foot characteristics including heel to toe, arch location, and width. These characteristics are then used to select an existing article of footwear. Other adjustments are often handled through a manual trial and error system in which a user tries on a pair of shoes and problems are resolved through making various adjustments. Unfortunately, this process is not reliable for addressing the needs of a user in adjusting or selecting appropriate footwear.

Therefore, there is a need in the industry for systems and methods of measuring and adjusting footwear to accommodate the unique podiatric needs of a user.

SUMMARY OF THE INVENTION

The present invention relates to footwear including shoes, boots, sandals, etc. In particular, the present invention relates to systems and methods for properly measuring, aligning, fitting, and adjusting feet and footwear. One embodiment of the present invention relates to a footwear characteristic measuring system designed to determine measurements of a particular footwear wedge insert which may be used to encourage correct knee alignment in an article of footwear. The system includes a base, a stepped member, a platform, and an illumination system. The stepped member or piano hinge is positioned on the top surface of the base adjacent to or partially under the platform. The platform is disposed above the top surface of the base and connected on a first side to the base via a hinge. A second portion of the platform is positioned on top of a portion of the stepped member so as to form a particular angle with respect to the base depending on the height of the particular stepped member surface. The illumination system is oriented to transmit an illumination output upward or perpendicular to the top surface of the base. A second embodiment of the present invention relates to a method of encouraging correct knee and ankle alignment in an article of footwear. The method includes transmitting an illumination device upward and articulating a user's knee and ankle until the user's knee is medially illuminated. If it is necessary to laterally articulate the user's ankle (varus or valgus), the method further includes incrementally positioning the platform on a higher stepped surface until the user's knee is illuminated without lateral ankle articulation, and positioning a corresponding angled member within an article of footwear so as to encourage proper knee alignment.

Embodiments of the present invention represent a significant advance in footwear measuring and fitting technology. Conventional systems and methods fail to accurately and reliably measure feet in relation to knee positioning for adjusting varus and valgus ankle articulation. Likewise, conventional footwear does not accommodate the unique varus and valgus slopes necessary to encourage proper alignment for numerous users.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

The following description of the invention can be understood in light of the Figures, which illustrate specific aspects of the invention and are a part of the specification. Together with the following description, the Figures demonstrate and explain the principles of the invention. In the Figures, the physical dimensions may be exaggerated for clarity. The same reference numerals in different drawings represent the same element, and thus their descriptions will be omitted.

DETAILED DESCRIPTION OF THE INVENTION

The present invention relates to footwear including shoes, boots, sandals, etc. In particular, the present invention relates to systems and methods for properly measuring, aligning, fitting, and adjusting feet and footwear. One embodiment of the present invention relates to a footwear characteristic measuring system designed to determine measurements of a particular footwear wedge insert which may be used to encourage correct knee alignment in an article of footwear. The system includes a base, a stepped member, a platform, and an illumination system. The stepped member or piano hinge is positioned on the top surface of the base adjacent to or partially under the platform. The platform is disposed above the top surface of the base and connected on a first side to the base via a hinge. A second portion of the platform is positioned on top of a portion of the stepped member so as to form a particular angle with respect to the base depending on the height of the particular stepped member surface. The illumination system is oriented to transmit an illumination output upward or perpendicular to the top surface of the base. A second embodiment of the present invention relates to a method of encouraging correct knee and ankle alignment in an article of footwear. The method includes transmitting an illumination device upward and articulating a user's knee and ankle until the user's knee is medially illuminated. If it is necessary to laterally articulate the user's ankle (varus or valgus), the method further includes incrementally positioning the platform on a higher stepped surface until the user's knee is illuminated without lateral ankle articulation, and positioning a corresponding angled member within an article of footwear so as to encourage proper knee alignment. Also, while embodiments are described in reference to footwear, it will be appreciated that the teachings of the present invention are application to other areas.

The following terms are defined as follows:

Footwear—Any type of covering, protecting, and/or supporting structure designed to at least partially cover the foot of a user including but not limited to shoes, sandals, boots, clogs, slippers, etc.

Correlated illumination device—An illumination device that produces a substantially correlated illumination output including but not limited to a laser and a bulb with a set of correlating optics.

Knee articulation—For purposes of this application the term "knee articulation" refers simple to bending of the knee in the medial plane. Any lateral knee articulation is discussed with reference to any associated lateral ankle articulation, as described below.

Ankle articulation—the human ankle is able to articulate in a plurality of directions and orientations. For purposes of this application, the term "lateral articulation" refers to varus and valgus articulation, also commonly associated with the terms supination and pronation. Non-lateral ankle articulation or otherwise non-designated ankle articulation refers to plantar flexion and dorsiflexion in the medial plane, also commonly associated with forward and rearward articulation.

Figure 1:
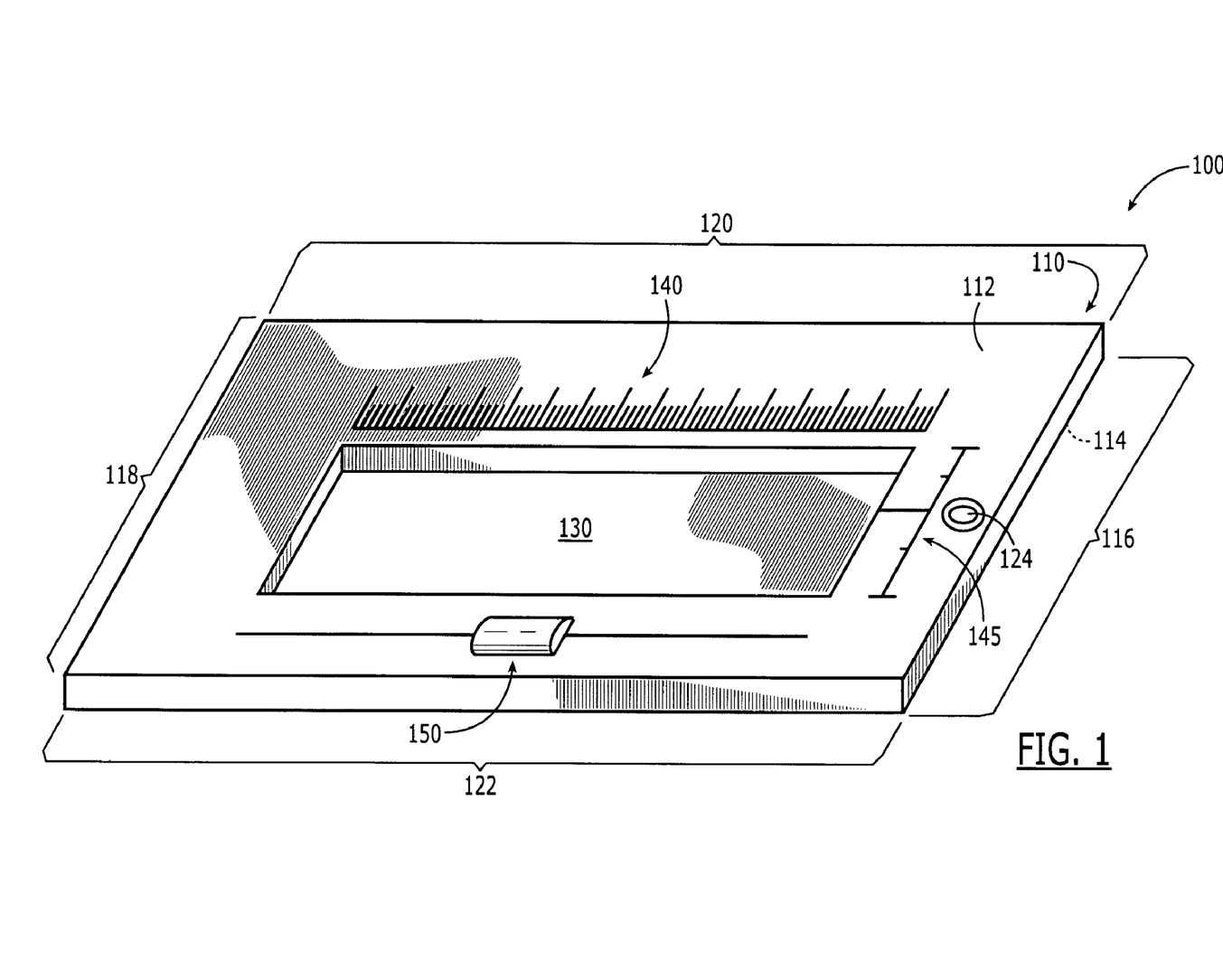
FIG. 1 illustrates a perspective view of a footwear characteristic measuring system in accordance with one embodiment of the present invention.

Reference is initially made to FIG. 1, which illustrates a perspective view of a footwear characteristic measuring system, designated generally at 100. The system 100 includes a base 110, a recess 130, a correlated illumination device 124, a plurality of angled members (illustrated and described with reference to FIG. 2), a length measurement system 140, a medial alignment system 145, and an arch height measurement system 150. The base 110 includes a top surface 112, a bottom surface 114, a front end 116, a rear end 118, a left medial side 120, and a right medial side. The base 110 may be composed of materials including metal and plastic. The recess 130 is disposed on the top surface 112 of the base 110 between the front and rear ends 116, 118 and may optionally extend through or up to the bottom surface 114. The correlated illumination device 124 is also disposed on the top surface 112 of the base 110 between the front and rear ends 116, 118. The recess 130 and the correlated illumination device 124 are medially aligned on the top surface 112 of the base 110 between the left and right medial sides 120, 122. The illustrated correlated illumination device 124 is a laser oriented upward and substantially perpendicular to the top surface 112 of the base 110. Although not illustrated, the correlated illumination device may include a power supply and electrical switching mechanism housed within the base 110. Various technologies and/or techniques may be utilized to produce a completely visible light beam including dust dispersement and/or low ambient lighting. Likewise, the bottom of the recess 130 may include a touch sensitive switching mechanism configured to automatically illuminate the correlated illumination device 124 in response to the weighting of the recess associated with a user positioning their foot within the recess 130 or on top of an angled member (See FIG. 2) disposed within the recess 130.

The optional length measurement system 140, medial alignment system 145, and arch height measurement system 150 are also disposed on the top surface 112 of the base 110 as illustrated. The length measurement system 140 includes a set of incremental length measurement marks along the corresponding left medial 120 side of the recess 130 incrementally ascending from the corresponding front side 116 of the recess 130. The function of the length measurement system 140 is to both measure the length of a user's foot disposed within the recess and encourage a repeatable placement/orientation of the user's foot in the recess. Likewise, the medial alignment system 145 is disposed on the corresponding front side 116 of the recess 130. The medial alignment system 145 includes a set of designation marks. The medial alignment system 145 functions as a medial or width measurement system of the user's foot in addition to encouraging proper medial alignment of the user's foot within the recess with respect to the left and right medial sides 120, 122. The arch height measurement system 150 is also disposed on the top surface 112 of the base 110 corresponding to the right medial side 122 of the recess 130. The arch height measurement system includes a slidably adjustable member that assists in reliably and accurately measuring the location of a foot's arch. The location of the slidable adjustable member may be correlated with the length measurement system's marks to identify the location of the arch with respect to the front of the foot.

Figure 2:
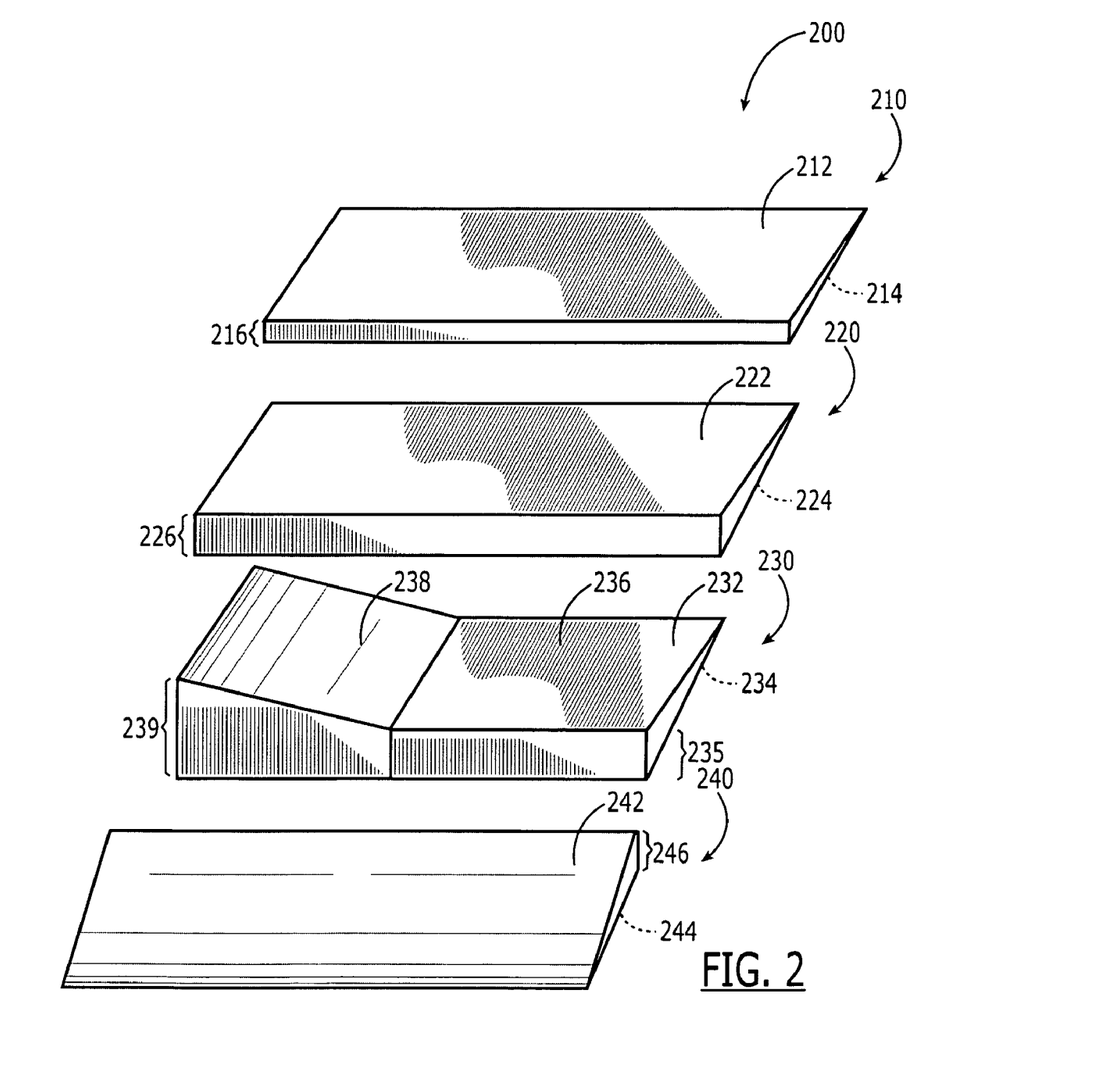
FIG. 2 illustrates a plurality of angled members for use in conjunction with the footwear measuring system illustrated in FIG. 1.

Reference is next made to FIG. 2, which illustrates a plurality of angled members for use in conjunction with the footwear measuring system illustrated in FIG. 1, designated generally at 200. The angled members 200 are configured to be releasably coupled within the recess 130 of the system 100. The angled members 200 are shaped so as to create a keyed releasable coupling with the recess for purposes of reliable and repeatable positioning and engagement. The angled members 200 are configured to support the weight of a user without significant deformation. The first angled member 210 includes a top surface 212, a bottom surface 214, and a wedge height 216. The wedge height 216 corresponds to the medial angle, creating a sloped top surface 212. The second angled member 220 also includes a top surface 222, a bottom surface 224, and a wedge height 226. It will be appreciated that the second angled member 220 has a larger wedge height 226 than the first angled member's 210 wedge height 216. The third angled member 230 includes a front component member 236 and a rear component member 238, a top surface 232, a bottom surface 234, a rear wedge height 239, and a front wedge height 235. The front and rear component members 236, 238 are shaped to facilitate the releasable keyed coupling with the recess 130 and one another. The rear component member 238 includes a lengthwise slope while the front component member 236 includes a lateral slope. Various wedge slope component members may be utilized in accordance with the teachings of the present invention. The fourth angled member 240 also includes a top surface 242, a bottom surface 244, and a wedge height 246. The fourth angled member 240 includes an oppositely oriented sloped top surface 242. Various alternative systems may be utilized so that individual angled members and components members may be rotated with respect to the recess so as to create a wide variety of sloped top surfaces.

Figure 3A:
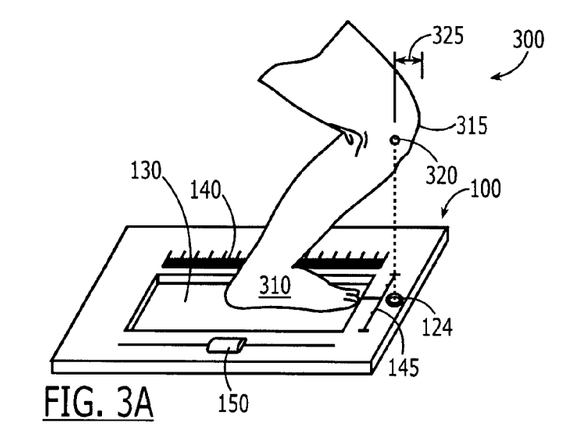
FIGS. 3A-3D illustrate a series of perspective views detailing a method of encouraging correct alignment in an article of footwear in accordance with a second embodiment of the present invention.
Figure 3B:
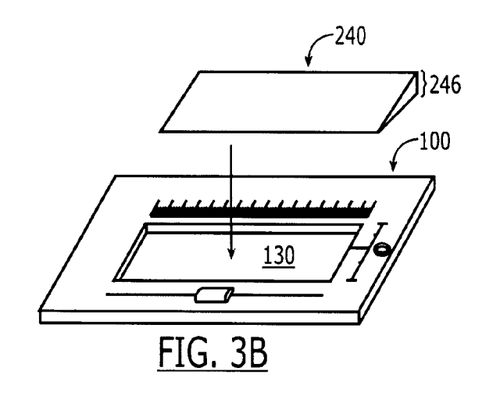
Figure 3C:
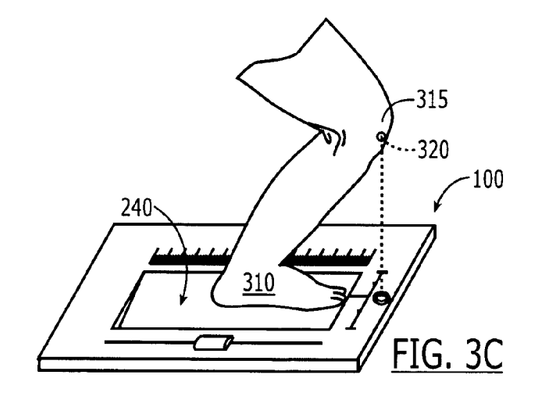
Figure 3D:
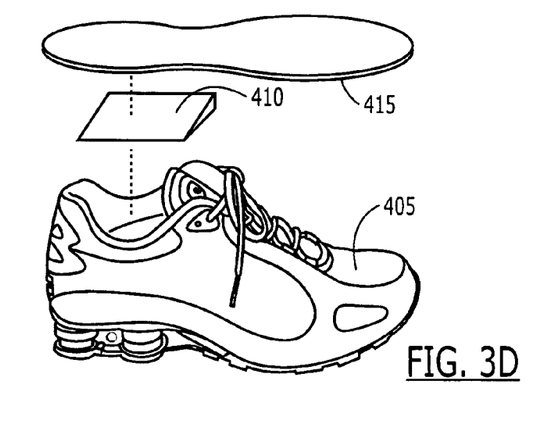

Reference is next made to FIGS. 3A-3D, which illustrate a series of perspective views detailing a method of encouraging correct alignment in an article of footwear. FIG. 3A illustrates a user's foot 310 positioned within the recess 130 of the system 100. The foot 310 is medially and frontward oriented with respect to the recess 130. The user's knee 315 is articulated to position the knee 315 in lengthwise orientation corresponding to the correlated illumination device 124. The correlated illumination device 124 created an illumination output 320 on the user's knee 315. In FIG. 3A the correlated illumination output 320 is medially offset from the center of the user's knee 315 a distance 325 and therefore would require a lateral ankle articulation to center the correlated illumination output 320 with respect to the user's knee. This indicates the need for some form of lateral ankle adjustment in the user's footwear to encourage proper alignment of the knee 315. FIG. 3B illustrates positioning an angled member 240 with a wedge height 246 within the recess 130 of the system 100. FIG. 3C then illustrates again positioning the user's foot 310 within the recess 130 on top of the angled member 240 and articulating the knee 315 and ankle forward to be illuminated by the correlated illumination output 320. As illustrated, the angled member 240 corrected the offset distance by medially aligning the correlated illumination output 320 with respect to the lateral location of the knee 315. Various iterations may be performed to select the proper angled member that best corrects the offset distance 325. FIG. 3D illustrates the positioning of a corresponding insert 410 within an article of footwear 405. The corresponding insert includes a wedge height corresponding to the wedge height 246 of the successfully angled member 240 that corrected the offset distance 325. The corresponding insert 410 is positioned between the internal removable sole 415 and the internal lower surface of the article of footwear 405. A subsequent process may be performed for the opposite foot. The internal removable sole 415 may include a region configured to receive the corresponding insert 410 so as to prevent lateral movement. The region may create a sandwiched, keyed coupling between the corresponding internal removable sole 415, the corresponding insert 410, and the internal lower surface of the article of footwear 405.

Figure 4:
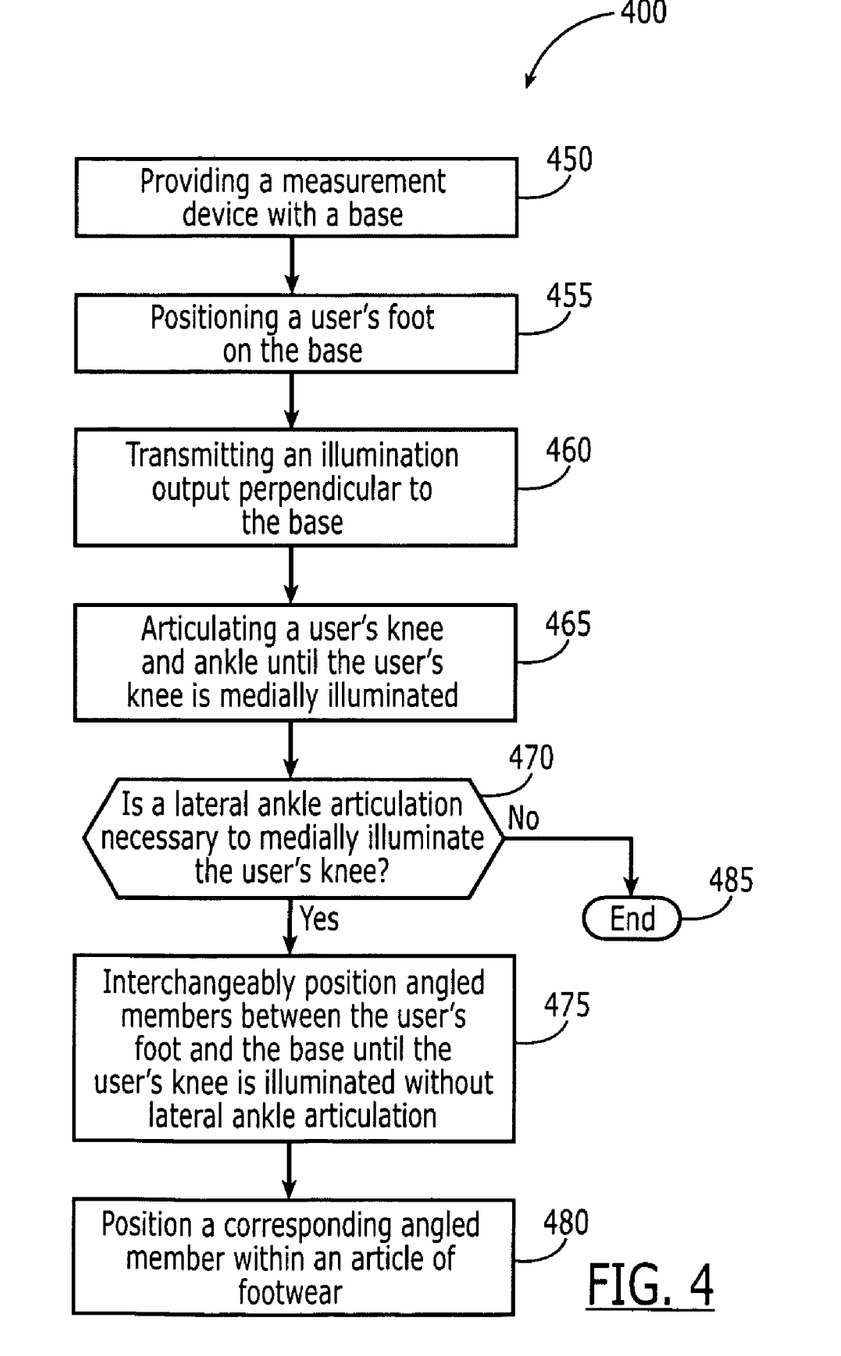
FIG. 4 illustrates a flow chart of a method of encouraging correct alignment in an article of footwear in accordance with a second embodiment of the present invention.

Reference is next made to FIG. 4, which illustrates a flow chart of a method of encouraging correct alignment in an article of footwear, designated generally at 400. First, providing a measurement device with a base, act 450. The measurement device may be the system illustrated in FIGS. 1-2. A user's foot is positioned on the base, act 455. An illumination output is transmitted perpendicular to the base, act 460. The user's knee and ankle are articulated to illuminate to the user's knee, act 465. A determination is made if it is necessary to laterally articulate the user's ankle to medially illuminate the user's knee, act 470. If the determination is affirmative, the method further includes interchangeably positioning angled members between the user's foot and the base until the user's knee is illuminated without lateral ankle articulation, act 475, and positioning a corresponding angled member within an article of footwear, act 480.

Reference is next made to FIGS. 5A-5D, which illustrate various views of an alternative footwear characteristic measuring system in accordance with embodiments of the present invention, designated generally at 500. The system 500 includes a base 505, a stepped member 520, a platform 510, and a correlated illumination system 550. The components move relative to one another and operate in conjunction to facilitate various measurements. The platform 510 further includes an incremental length measurement system 555, an arch height measurement system 535, a medial alignment system 545, and a gravitational leveling system 540. The base 505 is a rectangular shaped member with a lengthwise longer dimension and a widthwise narrower dimension corresponding to the orientations of the user's foot. The base 505 is elevated and supported via a plurality of adjustable supports 515. The supports 515 are screwed into bosses or recesses (not shown) on the bottom surface of the base 505 to enable adjusting the relative height at each of the corners. The base 505 may be composed of any substantially rigid material such as wood or metal.

The platform 510 is disposed on the top surface of the base 505 in an overlapping configuration in which the lengthwise and widthwise orientations of the platform 510 correspond with the lengthwise and widthwise orientations of the bases 505. The operation of the system 500 requires that the platform 510 be able to tilt widthwise, angle, or articulate with respect to the base 5050. The platform 510 may be coupled to base 505 via a hinge 507 (see FIG. 5D) or may simply utilize a gravitational type coupling. It will be noted that the thickness of the hinge 507 affects the normal or 0 degree positioning of the opposite side of the platform 510 relative to the base 505. In the illustrated embodiment, the stepped member 520 includes a first stepped surface 522 configured to correspond to the thickness of the hinge 507, thereby creating a flat or level 0 degree orientation of the platform 510 with respect to the base 505.

The platform 510 includes an arch height measurement system 535. As described above with reference to element 150 on FIG. 1, the arch height measurement system 535 includes a lengthwise sliding member and a visual height indicator. The sliding member is coupled to the platform 510 via a magnetic coupling that substantially maintains a particular widthwise alignment. The visual height indicator includes uniquely color coded levels corresponding to particular arch heights. The colors on the visual height indicator may correspond to particular arch support inserts which may be utilized in proper fitting of footwear.

The platform 510 also includes an incremental length measurement system 555 and a medial alignment system 545 configured to operate in conjunction to measure the length of a user's foot. In the illustrated embodiment, the incremental length measurement system 555 and the medial alignment system 545 are multi-directional, meaning that they may be used to measure a user's foot along either of the two lengthwise orientations of the platform 510. It will be appreciated that a uni-directional system may also be utilized in accordance with embodiments of the present invention. The medial alignment system 545 includes two heel cups to receive a user's heel for alignment purposes. The incremental length measurement system 555 includes a visual indicator of mens and womens footwear sizes, increasing from each of the heel cups.

The platform 510 also includes a gravitational leveling system 540 which may be used to initially level the base 505 and platform 510 before measuring a user's foot. The illustrated gravitational leveling system 540 includes a two dimensional bubble level or bulls-eye type bubble level which visually shows if the system 500 is tilted in any two dimensional direction relative to the ground or supporting surface. Any tilt may then be eliminated through incremental height adjustments of the supports 515 below the base 505. Various other leveling systems may be utilized such as multiple one dimensional bubble levels, electronic gyroscopic levels, etc.

Figure 5A:
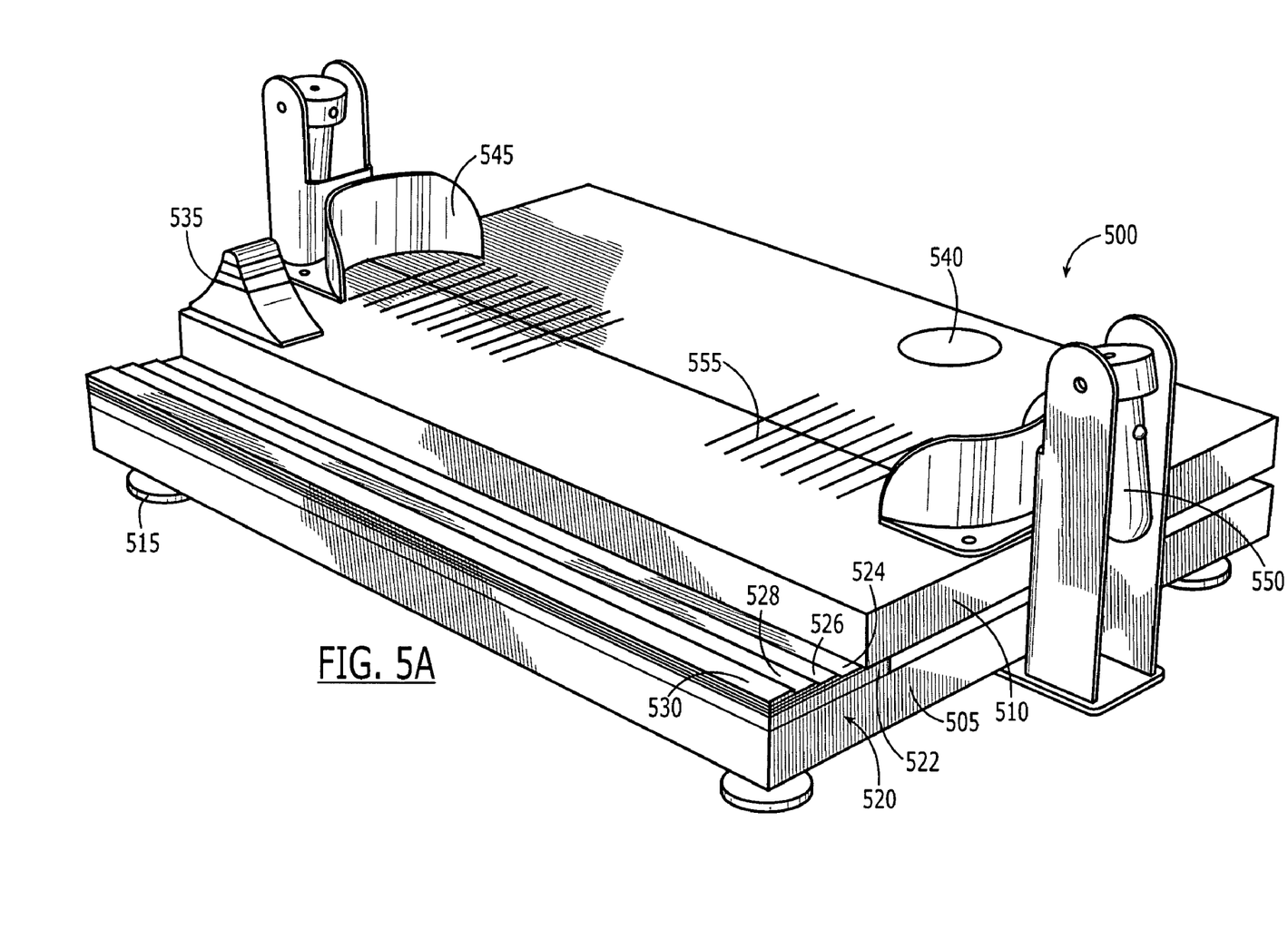
FIGS. 5A-5D illustrate various views of an alternative footwear characteristic measuring system in accordance with embodiments of the present invention.
Figure 5B:
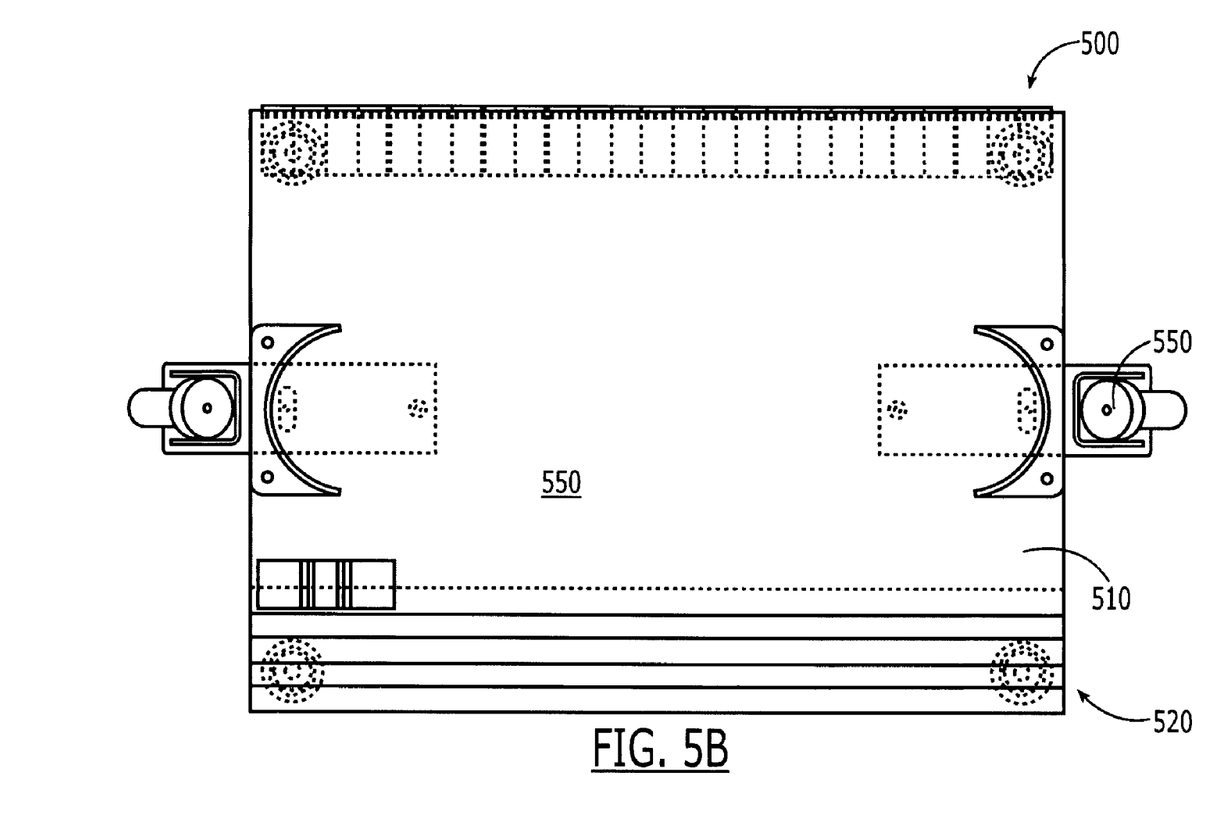
Figure 5C:
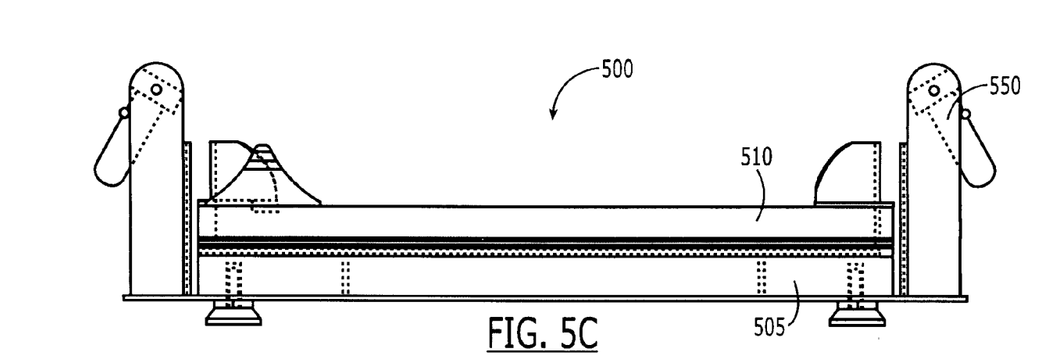
Figure 5D:
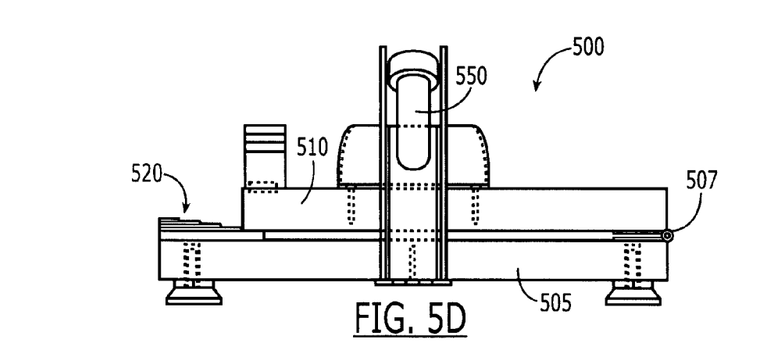

The stepped member 520 is positioned on the top surface of the base 505 in a lengthwise orientation substantially adjacent or overlapping with the platform 510. The stepped member 520 includes a plurality of stepped surfaces 522, 524, 526, 528, 530 that are incrementally thicker with respect to one another. The plurality of stepped surfaces 522, 524, 526, 528, 530 increase in thickness incrementally relative to their spacing away from the platform 510. The plurality of stepped surfaces 522, 524, 526, 528, 530 may be created by stacking or tiling elements on top of one another in a cascading configuration as illustrated. Alternatively, the stepped surfaces 522, 524, 526, 528, 530 may be created by a solid stepped member 520. Each of the stepped surfaces 522, 524, 526, 528, 530 is uniquely color coded or indicated so as to correspond to a particular tilt angle between the platform 510 and the base 505. FIG. 5A illustrates the platform 510 being disposed on the bottom stepped surface 522 corresponding to a 0 degree tilt. The stepped member 520 is configured to widthwise translate across the base 505 so as to position a different stepped surface under the platform 510 and adjust the tilt angle respectively. The operation and configuration of the stepped member 520 and platform 510 may be referred to as a piano hinge in that the stepped surfaces incrementally scale/step up the tilt between the platform 510 and the base 505. In addition, the stepped surfaces are visually similar to a set of piano keys.

The correlated illumination system 550 is coupled to the base 505. The correlated illumination system 550 includes two lasers coupled to two support members. The lasers are configured to generate a correlated illumination output (any laser beam) along a plane normal to the top surface of the base 505. In addition, the support members of the system 550 are configured to hold the laser in a particular orientation for operation of the system 550. The illustrated lasers may be semiconductor type red lasers or the like. The support members are coupled to the bottom surface of the base 505 and include a housing which extends vertically from the base 505 above the platform 510 on either widthwise side of the lasers to facilitate the vertical articulation. The coupling between the lasers and the housing may include some form of rubber o-ring to support the lasers in a selected orientation. The correlated illumination system 550 is positioned on the base 505 so as to medially align with the medial alignment system 545 of the platform 510. The illustrated correlated illumination system 550 is multi-directional and includes two lasers, but it will be appreciated that a uni-directional system may also be utilized.

Figure 6:
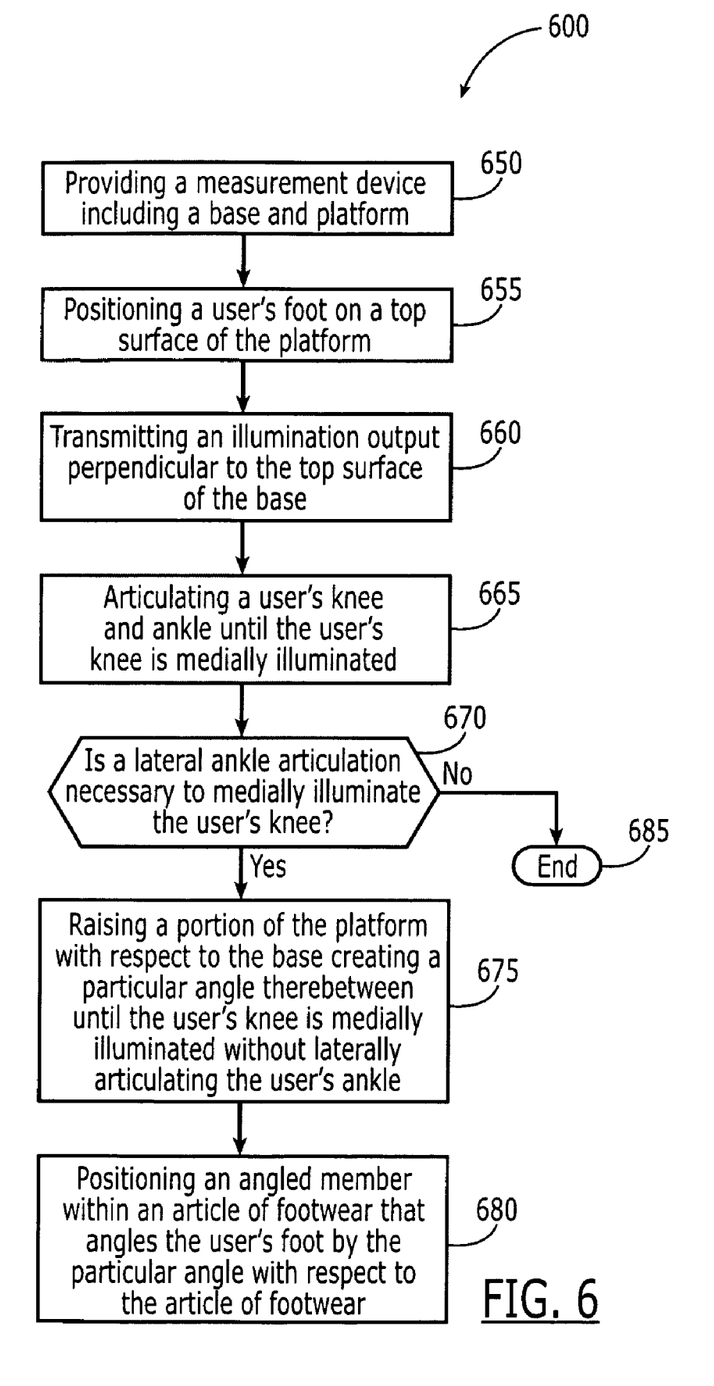
FIG. 6 illustrates a flow chart of a method of encouraging correct alignment in an article of footwear in accordance with the embodiment illustrated in FIGS. 5A-5D of the present invention.

Reference is next made to FIG. 6, which illustrates a flow chart of a method of encouraging correct alignment in an article of footwear, designated generally at 400. The method is described in correspondence with the components of the system embodiment illustrated in FIG. 5A-D, but it will be appreciated that a similar method may be utilized in conjunction with the embodiments illustrated in FIGS. 1-3. A measurement device with a base and platform is provided, act 450. The measurement device may be the system illustrated in FIGS. 5A-5D. The measurement device may be normalized or leveled to ensure that it is accurate. For example, the gravitational leveling system 540 and the adjustable supports 515 may be utilized to facilitate this function. A user's foot is positioned on a top surface of the platform, act 455. The user's foot is medially aligned on the platform 510 by positioning the user's foot within one of the heel cups of the medial alignment system 545. At this stage, the length of the user's foot may be accurately measured with the length measurement system 555. In addition, the arch height of the user's foot may be accurately measured with the arch height measurement system 535. An illumination output is transmitted perpendicular to the top surface of the base, act 460. The illumination output is generated by turning on the laser and orienting the laser upward to correspond with the angle and height of the user's knee. The user's knee and ankle are articulated to illuminate to the user's knee, act 465. A determination is made if it is necessary to laterally articulate the user's ankle to medially illuminate the user's knee, act 470. If the determination is affirmative, the method further includes raising or tilting a portion of the platform 510 with respect to the base 505 thereby creating a particular angle therebetween until the user's knee is illuminated without lateral ankle articulation, act 475. As described above, the raising of the platform 510 with respect to the base 505 includes translating the stepped member 520 below the platform 510 so as to position an increased height stepped surface 522, 524, 526, 528, 530 between the platform 510 and the base 505. Once the proper angle or stepped surface is determined that properly aligns the laser with the user's knee, a corresponding angled member or insert may be selected for use in the user's footwear. Positioning an angled member within an article of footwear that angles the user's foot by the particular angle with respect to the article of footwear, act 480. The stepped surfaces 522, 524, 526, 528, 530 may be uniquely color coded to match particular footwear inserts that generate a similar tilt angle within the user's footwear to that between the platform 510 and base 505.

What is claimed is:

1. A footwear characteristic measuring system comprising:
a base having a top surface;
a stepped member disposed on the top surface of the base, wherein the stepped member includes a plurality of stepped surfaces each of which are substantially parallel to the top surface of the base, and wherein each of the stepped surfaces is a particular height above the base;
a platform disposed above the top surface of the base, wherein a first portion of the platform is configured to be disposed on at least one of the top surface of the base and one of the plurality of stepped surfaces, and wherein a second portion of the platform is configured to be coupled to the base, and wherein a particular angle is formed with respect to the first and second portions of the platform and the base corresponding to disposition of the first portion of the platform with respect to the base and stepped surfaces;

wherein the stepped member is configured to translate with respect to the base so as to adjust the particular stepped surface between the first portion of the platform and the base thereby effecting the particular angle; and a correlated illumination system coupled to the base, wherein the correlated illumination device is configured to generate a correlated illumination output substantially perpendicular to the top surface of the base.

2. The system of claim 1, wherein the coupling between the platform and the base includes a hinge.

3. The system of claim 1, wherein the coupling between the platform and the base includes a gravitational coupling.

4. The system of claim 1, wherein the base further includes a plurality of adjustable supports configured to support a lower surface of the base above a support surface.

5. The system of claim 1, wherein the stepped member is oriented and configured on the top surface of the base such that the plurality of stepped surfaces increase in height above the base in conjunction with increasing in translational spacing from the first portion of the platform.

6. The system of claim 1, wherein the platform further includes a dual directional incremental length measurement system ascending from two lengthwise ends of a top surface of the platform.

7. The system of claim 1, wherein platform further includes an arch height measurement system, and wherein the arch height measurement system includes a lengthwise translation member that is translationally coupled to the platform and a visual height indicator thereupon.

8. The system of claim 1, wherein the platform further includes a medial alignment system including a heel cup that is configured to align a user's foot with the correlated illumination device with respect to the base.

9. The system of claim 1, wherein the correlated illumination system includes at least one laser, and wherein the at least one laser is configured to articulate within a plane substantially perpendicular to the base.

10. The system of claim 1, wherein the platform further includes a gravitational level indication system.

11. The system of claim 10, wherein the gravitational level indication system includes a bubble type level and plurality of adjustable supports on a lower surface of the base.

12. The system of claim 1, wherein the correlated illumination system further includes:
an illumination component configured to electrically generate an illumination output;
an electrical switching mechanism to select between an on and off state; and
a power supply electrically coupled to the illumination component and the electrical switching mechanism.

13. A footwear characteristic measuring system comprising:
a base having a top surface;
a stepped member lengthwise disposed on the top surface of the base, wherein the stepped member includes a plurality of stepped surfaces each of which are substantially parallel to the top surface of the base, and wherein each of the stepped surfaces is a particular height above the base;
a platform lengthwise disposed on the top surface of the base, wherein a first portion of the platform is configured to be disposed on one of the plurality of stepped surfaces, and wherein a second portion of the platform is configured to be hingably coupled to the base, and wherein a particular angle is formed with respect to the first and second portions of the platform and the base corresponding to disposition of the first portion of the platform with respect to the base and stepped surfaces;

wherein the stepped member is configured to widthwise translate with respect to the base so as to effectuate the particular stepped surface upon which the first portion of the platform is disposed thereby effecting the particular angle; and a correlated illumination system coupled to the base, wherein the correlated illumination device is configured to generate a correlated illumination output substantially perpendicular to the top surface of the base.

14. A method of encouraging correct alignment in an article of footwear including the acts of:
providing a measurement device including a base and a platform;
positioning a user's foot on a top surface of the platform;
transmitting an illumination output perpendicular to the top surface of the base;
articulating the user's knee and ankle until the user's knee is medially illuminated;
if a lateral articulation of the user's ankle is necessary to medially illuminate the user's knee, performing the following acts:
raising a portion of the platform with respect to the base creating a particular angle therebetween until the user's knee is medially illuminated without laterally articulating the user's ankle; and
positioning an angled member within an article of footwear that angles the user's foot by the particular angle with respect to the article of footwear.

15. The method of claim 14, wherein the act of providing a measurement device further includes providing a footwear characteristic measuring system comprising:
a base having a top surface;
a stepped member disposed on the top surface of the base, wherein the stepped member includes a plurality of stepped surfaces each of which are substantially parallel to the top surface of the base, and wherein each of the stepped surfaces is a particular height above the base;
a platform disposed on the top surface of the base, wherein a first portion of the platform is configured to be disposed on at least one of the base and one of the plurality of stepped surfaces, and wherein a second portion of the platform is configured to be coupled to the base, and wherein a particular angle is formed with respect to the first and second side of the platform and the base corresponding to disposition of the first portion of the platform with respect to the base and stepped surfaces;

wherein the stepped member is configured to translate with respect to the base so as to effectuate the particular stepped surface upon which the first portion of the platform is disposed thereby effecting the particular angle; and a correlated illumination system coupled to the base, wherein the correlated illumination device is configured to generate a correlated illumination output substantially perpendicular to the top surface of the base and substantially medially aligned with an orientation of the top surface of the base.

16. The method of claim 14, wherein the act of positioning a user's foot on a top surface of the platform includes medially aligning the user's foot with respect to a correlated illumination system of the measurement device.

17. The method of claim 16, wherein the act of positioning an angled member within an article of footwear that angles the user's foot by the particular angle with respect to the article of footwear, further includes positioning the final angled member between an internal removable sole and an internal base of an article of footwear.

18. The method of claim 14 further including two dimensionally leveling the base and platform with a gravitational type level.

19. The method of claim 14, wherein the act of positioning a user's foot on a top surface of the platform includes measuring the length and arch height of the user's foot with a lengthwise measurement system and arch height measurement system disposed on the platform.

20. The method of claim 14, wherein the act of raising a portion of the platform with respect to the base creating a particular angle therebetween until the user's knee is medially illuminated without laterally articulating the user's ankle further includes incrementally translating a stepped member between the base and platform.

* * * * *